United States Patent
Govari et al.

(10) Patent No.: US 11,413,098 B2
(45) Date of Patent: Aug. 16, 2022

(54) SEMI-AUTOMATED ABLATION SYSTEM

(71) Applicant: Biosense Webster (Israel) Ltd., Yokneam (IL)

(72) Inventors: Assaf Govari, Haifa (IL); Ella Ozeri, Binyamina (IL); Andres Claudio Altmann, Haifa (IL); Shimon Miara, Haifa (IL); Israel Zilberman, Yokneam (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 914 days.

(21) Appl. No.: 16/213,613

(22) Filed: Dec. 7, 2018

(65) Prior Publication Data
US 2020/0179063 A1    Jun. 11, 2020

(51) Int. Cl.
*A61B 34/00* (2016.01)
*A61B 18/14* (2006.01)
(Continued)

(52) U.S. Cl.
CPC .......... *A61B 34/25* (2016.02); *A61B 18/1492* (2013.01); *A61B 2017/00199* (2013.01);
(Continued)

(58) Field of Classification Search
None
See application file for complete search history.

(56) References Cited

U.S. PATENT DOCUMENTS 7,536,218 B2   5/2009   Govari et al.
7,756,576 B2   7/2010   Levin
(Continued)

FOREIGN PATENT DOCUMENTS

| EP | 2338428 A1 | 6/2011 | |
|---|---|---|---|
| WO | WO2010064154 A1 | 6/2010 | |
| WO | WO-2018200865 A1 * | 11/2018 | ............. A61B 18/02 |
| WO | WO2018200865 A1 | 11/2018 | |

OTHER PUBLICATIONS

Hussein, A. et al., "Ablation Index-Guided Pulmonary Vein Isolation for Atrial Fibrillation May Improve Clinical Outcomes in Comparison to Contact Force-Guided Ablation", Heart Rhythm Congress, Feb. 6, 2018, p. 33.
(Continued)

*Primary Examiner* — Ronald Hupczey, Jr.

(57) ABSTRACT

In one embodiment, an ablation system includes a probe to be inserted into a heart and including an electrode to apply radiofrequency (RF) power so as to ablate a myocardium, an RF signal generator, a tracking module to compute a relative location and orientation of the probe, and a processor to receive a signal from at least one user input device indicating an actuation of a serial ablation procedure including performing ablations at different locations of the myocardium, and control the serial ablation procedure so that for each ablation the processor is configured to check whether the relative location and orientation of the probe are steady, automatically compute an ablation duration, automatically control the RF signal generator to generate the RF power for the computed ablation duration, and render a user interface screen including a time indicator indicating a time remaining until an end of the ablation duration.

30 Claims, 9 Drawing Sheets

(51) Int. Cl.
*A61B 34/10* (2016.01)
*A61B 34/20* (2016.01)
*A61B 90/00* (2016.01)
*A61B 17/00* (2006.01)
*A61B 18/00* (2006.01)
*G06T 11/00* (2006.01)
*G06T 11/60* (2006.01)

(52) U.S. Cl.
CPC ............... *A61B 2018/00357* (2013.01); *A61B 2018/00577* (2013.01); *A61B 2018/00702* (2013.01); *A61B 2018/00761* (2013.01); *A61B 2018/00791* (2013.01); *A61B 2018/00839* (2013.01); *A61B 2018/00875* (2013.01); *A61B 2018/00886* (2013.01); *A61B 2018/00904* (2013.01); *A61B 2034/107* (2016.02); *A61B 2034/2065* (2016.02); *A61B 2034/252* (2016.02); *A61B 2090/064* (2016.02); *A61B 2218/002* (2013.01); *G06T 11/001* (2013.01); *G06T 11/60* (2013.01); *G06T 2200/24* (2013.01); *G06T 2210/41* (2013.01)

(56) References Cited

U.S. PATENT DOCUMENTS

| 9,662,170 | B2* | 5/2017 | Budzelaar | A61B 8/0883 |
| 2007/0060832 | A1 | 3/2007 | Levin | |
| 2011/0152856 | A1 | 6/2011 | Govari et al. | |
| 2012/0029504 | A1 | 2/2012 | Afonso et al. | |
| 2013/0116681 | A1 | 5/2013 | Zhang | |
| 2016/0113709 | A1* | 4/2016 | Maor | A61B 18/1492 606/41 |
| 2017/0014181 | A1 | 1/2017 | Bar-Tai et al. | |
| 2017/0156792 | A1* | 6/2017 | Ziv-Ari | A61B 18/1492 |
| 2018/0263690 | A1 | 9/2018 | Govari et al. | |

OTHER PUBLICATIONS

Pending U.S. Appl. No. 15/896,687, filed Feb. 14, 2018.
European Search Report for corresponding EPA No. 19214230.5 dated Apr. 14, 2020.

* cited by examiner

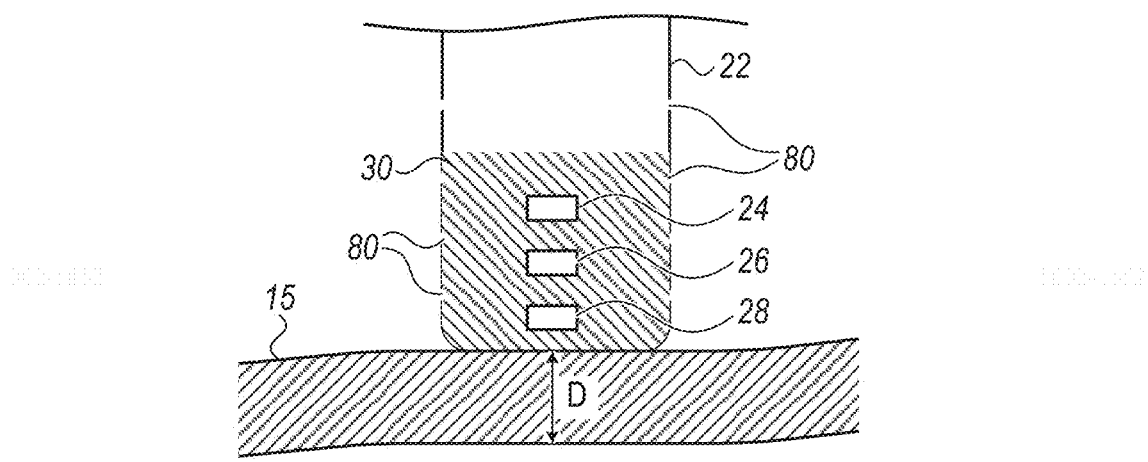
FIG. 2
FIG. 3
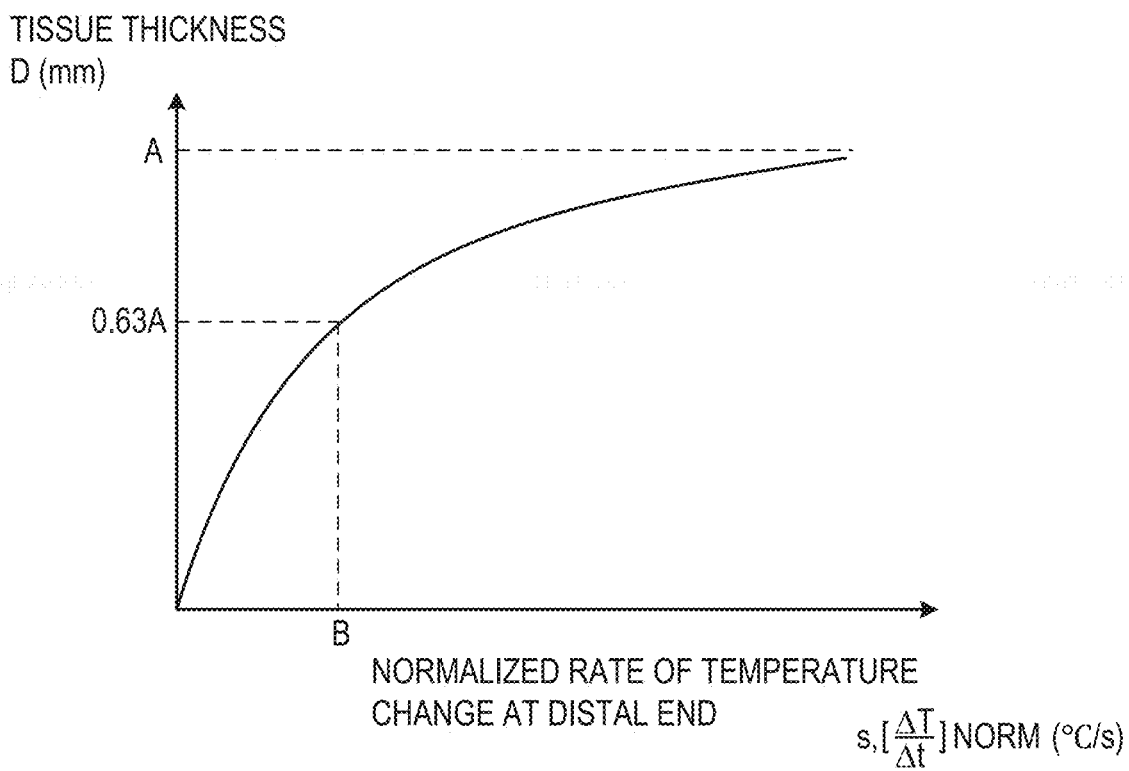

SEMI-AUTOMATED ABLATION SYSTEM

FIELD OF THE INVENTION

The present invention relates to medical systems, and in particular, to systems to perform ablation.

BACKGROUND

Ablation of tissue, such as ablation performed by injecting radiofrequency (RF) power into the tissue, is a well-known procedure that is used, for example, to correct defects in the heart. Typically, in these cases the ablation is used to inactivate selected groups of cells in the myocardium, so that they no longer transfer an electropotential wave in the myocardium. Multiple ablation sites may be targeted with RF power as part of a corrective procedure.

US Patent Publication 2013/0116681 of Zhang describes a system providing heart ablation unit control and including an input processor for acquiring electrophysiological signal data from multiple tissue locations of a heart and data indicating tissue thickness at the multiple tissue locations. A signal processor processes the acquired electrophysiological signal data to identify location of particular tissue sites of the multiple tissue locations exhibiting electrical abnormality in the acquired electrophysiological signal data and determines an area of abnormal tissue associated with individual sites of the particular sites. An ablation controller automatically determines ablation pulse characteristics for use in ablating cardiac tissue at an individual site of the particular tissue sites in response to the acquired data indicating the thickness of tissue and determined area of abnormality of the individual site.

US Patent Publication 2011/0152856 of Govari, et al., describes tissue ablation systems and methods, wherein a cardiac catheter incorporates a pressure detector for sensing a mechanical force against the distal tip when engaging an ablation site. Responsively to the pressure detector, a controller computes an ablation volume according to relationships between the contact pressure against the site, the power output of an ablator, and the energy application time. A monitor displays a map of the heart which includes a visual indication of the computed ablation volume. The monitor may dynamically display the progress of the ablation by varying the visual indication.

US Patent Publication 2012/0029504 of Afonso, et al., describes a method and system for presenting information representative of lesion formation. The system comprises an electronic control unit (ECU). The ECU is configured to acquire a value for an ablation description parameter and/or a position signal metric, wherein the value corresponds to a location in the tissue. The ECU is further configured to evaluate the value, assign it a visual indicator of a visualization scheme associated with the parameter/metric corresponding to the value, and generate a marker comprising the visual indicator such that the marker is indicative of the acquired value. The method comprises acquiring a value for the parameter/metric, and evaluating the value. The method further includes assigning a visual indicator of a visualization scheme associated with the parameter/metric corresponding to the value, and generating a marker comprising the visual indicator.

SUMMARY

There is provided in accordance with an embodiment of the present disclosure, an ablation system including a probe configured to be inserted into a chamber of a heart, the probe including an electrode configured to apply radiofrequency (RF) power to a myocardium in the chamber so as to ablate the myocardium, an RF signal generator configured to generate the RF power to be applied by the electrode to ablate the myocardium, a tracking module configured to compute a relative location and a relative orientation of the probe, a user interface including at least one user input device and a display, and a processor configured to receive a signal from the at least one user input device indicating an actuation of a serial ablation procedure including performing a plurality of ablations over time at different locations of the myocardium, and control the serial ablation procedure responsively to receiving the signal so that for each one ablation of the plurality of ablations the processor is configured to check whether the relative location and the relative orientation of the probe are steady to within a given tolerance for a given time period prior to the one ablation, automatically compute an ablation duration for the one ablation after finding the probe to be steady at the relative location, automatically control the RF signal generator to generate the RF power for the computed ablation duration of the one ablation, and render to the display a user interface screen including a plurality of indicators describing a state of the serial ablation procedure, the plurality of indicators including a time indicator indicating a time remaining until an end of the ablation duration at the relative location.

Further in accordance with an embodiment of the present disclosure the processor is configured to compute a thickness of the myocardium at the relative location of each ablation of the plurality of ablations responsively to the probe being steady, and compute the ablation duration for each ablation responsively to the computed thickness.

Still further in accordance with an embodiment of the present disclosure the processor is configured to check whether the relative location of the probe is far enough away from a previous ablation prior to permitting performance of the one ablation.

Additionally, in accordance with an embodiment of the present disclosure the previous ablation was performed immediately prior to a current ablation under consideration.

Moreover, in accordance with an embodiment of the present disclosure the previous ablation was performed in a different serial ablation procedure.

Further in accordance with an embodiment of the present disclosure the processor is configured to check whether the relative location of the probe is close enough to a planned ablation site prior to permitting performance of each ablation of the plurality of ablations.

Still further in accordance with an embodiment of the present disclosure the processor is configured to receive a signal from the at least one user input device indicating selection of any one or more of the following planned ablation sites, a planned ablation area, and a planned ablation line having respective locations on a map of the myocardium.

Additionally, in accordance with an embodiment of the present disclosure the processor is configured to check whether sufficient time has elapsed since a previous ablation prior to permitting performance of the one ablation.

Moreover, in accordance with an embodiment of the present disclosure the processor is configured to check whether a force applied by the probe to the myocardium is within a given range prior to permitting performance of each ablation of the plurality of ablations.

Further in accordance with an embodiment of the present disclosure the processor is configured to halt the serial ablation procedure responsively to not receiving the signal from the at least one user input device.

Still further in accordance with an embodiment of the present disclosure the probe includes an irrigation channel through which to irrigate the myocardium, the system further including a pump to pump an irrigation fluid into the irrigation channel at an idle rate and at least one non-idle rate being higher than the idle rate, the processor being configured to control the pump to return to pumping at the idle rate when a waiting time between adjacent ones of the plurality of ablations is greater than a given time period.

Additionally, in accordance with an embodiment of the present disclosure the processor is configured to generate, and render to the display, the user interface screen showing an indicator moving along a line indicative of the time remaining until an end of the waiting time period.

Moreover, in accordance with an embodiment of the present disclosure the probe includes a temperature sensor configured to provide a temperature signal which is indicative of a temperature of the myocardium at a plurality of different times, the processor being configured to generate, and render to the display, the user interface screen showing a colored area having a color indicative of the temperature of the myocardium.

Further in accordance with an embodiment of the present disclosure the processor is configured to generate, and render to the display, the user interface screen showing a colored area having a color indicative of an impedance measurement of the myocardium.

Still further in accordance with an embodiment of the present disclosure the processor is configured to generate, and render to the display, the user interface screen showing an indicator moving along a line indicative of the time remaining until the end of the ablation duration.

Additionally, in accordance with an embodiment of the present disclosure the processor is configured to generate, and render to the display, the user interface screen showing any one or more of the following a temperature of the myocardium, an impedance of the myocardium, a change in the impedance of the myocardium, the ablation duration, a thickness of the myocardium, an irrigation rate symbol, and an ablation number in the serial ablation procedure.

There is also provided in accordance with another embodiment of the present disclosure, an ablation method including computing a relative location and a relative orientation of a probe configured to be inserted into a chamber of a heart, the probe including an electrode configured to apply radiofrequency (RF) power to a myocardium in the chamber so as to ablate the myocardium, receiving a signal from at least one user input device indicating an actuation of a serial ablation procedure including performing a plurality of ablations over time at different locations of the myocardium, and controlling the serial ablation procedure responsively to receiving the signal so that for each one ablation of the plurality of ablations the following are performed checking whether the relative location and the relative orientation of the probe are steady to within a given tolerance for a given time period prior to the one ablation, automatically computing an ablation duration for the one ablation after finding the probe to be steady at the relative location, automatically controlling the RF signal generator to generate the RF power for the computed ablation duration of the one ablation, and rendering to a display a user interface screen including a plurality of indicators describing a state of the serial ablation procedure, the plurality of indicators including a time indicator indicating a time remaining until an end of the ablation duration at the relative location.

Moreover, in accordance with an embodiment of the present disclosure, the method includes computing a thickness of the myocardium at the relative location of each ablation of the plurality of ablations responsively to the probe being steady, wherein computing the ablation duration includes computing the ablation duration for each ablation responsively to the computed thickness.

Further in accordance with an embodiment of the present disclosure, the method includes checking whether the relative location of the probe is far enough away from a previous ablation prior to permitting performance of the one ablation.

Still further in accordance with an embodiment of the present disclosure the previous ablation was performed immediately prior to a current ablation under consideration.

Additionally, in accordance with an embodiment of the present disclosure the previous ablation was performed in a different serial ablation procedure.

Moreover, in accordance with an embodiment of the present disclosure, the method includes checking whether the relative location of the probe is close enough to a planned ablation site prior to permitting performance of each ablation of the plurality of ablations.

Further in accordance with an embodiment of the present disclosure, the system includes receiving a signal from the at least one user input device indicating selection of any one or more of the following planned ablation sites, a planned ablation area, and a planned ablation line, having respective locations on a map of the myocardium.

Still further in accordance with an embodiment of the present disclosure, the method includes checking whether sufficient time has elapsed since a previous ablation prior to permitting performance of the one ablation.

Additionally, in accordance with an embodiment of the present disclosure, the method includes checking whether a force applied by the probe to the myocardium is within a given range prior to permitting performance of each ablation of the plurality of ablations.

Moreover, in accordance with an embodiment of the present disclosure, the method includes halting the serial ablation procedure responsively to not receiving the signal from the at least one user input device.

Further in accordance with an embodiment of the present disclosure, the method includes pumping an irrigation fluid into an irrigation channel of the probe at an idle rate and at least one non-idle rate being higher than the idle rate, and controlling pumping of the irrigation rate to return to pumping at the idle rate when a waiting time between adjacent ones of the plurality of ablations is greater than a given time period.

Still further in accordance with an embodiment of the present disclosure, the method includes generating, and rendering to the display, the user interface screen showing an indicator moving along a line indicative of the time remaining until an end of the waiting time period.

Additionally, in accordance with an embodiment of the present disclosure, the method includes providing a temperature signal which is indicative of a temperature of the myocardium at a plurality of different times, and generating, and rendering to the display, the user interface screen showing a colored area having a color indicative of the temperature of the myocardium.

Moreover, in accordance with an embodiment of the present disclosure, the method includes generating, and rendering to the display, the user interface screen showing a colored area having a color indicative of an impedance measurement of the myocardium.

Further in accordance with an embodiment of the present disclosure, the method includes generating, and rendering to the display, the user interface screen showing an indicator moving along a line indicative of the time remaining until the end of the ablation duration.

Still further in accordance with an embodiment of the present disclosure, the method includes generating, and rendering to the display, the user interface screen showing any one or more of the following a temperature of the myocardium, an impedance of the myocardium, a change in the impedance of the myocardium, the ablation duration, a thickness of the myocardium, an irrigation rate symbol, and an ablation number in the serial ablation procedure.

There is also provided in accordance with still another embodiment of the present disclosure a software product, including a non-transient computer-readable medium in which program instructions are stored, which instructions, when read by a central processing unit (CPU), cause the CPU to compute a relative location and a relative orientation of a probe configured to be inserted into a chamber of a heart, the probe including an electrode configured to apply radiofrequency (RF) power to a myocardium in the chamber so as to ablate the myocardium, receive a signal from at least one user input device indicating an actuation of a serial ablation procedure including performing a plurality of ablations over time at different locations of the myocardium, and control the serial ablation procedure responsively to receiving the signal so that for each one ablation of the plurality of ablations the CPU is configured to check whether the relative location and the relative orientation of the probe are steady to within a given tolerance for a given time period prior to the one ablation, automatically compute an ablation duration for the one ablation after finding the probe to be steady at the relative location, automatically control an RF signal generator to generate the RF power for the computed ablation duration of the one ablation, and render to a display a user interface screen including a plurality of indicators describing a state of the serial ablation procedure, the plurality of indicators including a time indicator indicating a time remaining until an end of the ablation duration at the relative location.

BRIEF DESCRIPTION OF THE DRAWINGS

The present invention will be understood from the following detailed description, taken in conjunction with the drawings in which:

FIG. 2 is a schematic illustration of a distal end of a probe used in the apparatus of FIG. 1;

FIG. 3 is a graph of tissue thickness against a normalized rate of temperature change at the distal end of the probe of FIG. 2;

DESCRIPTION OF EXAMPLE EMBODIMENTS

Overview

Figure 1:
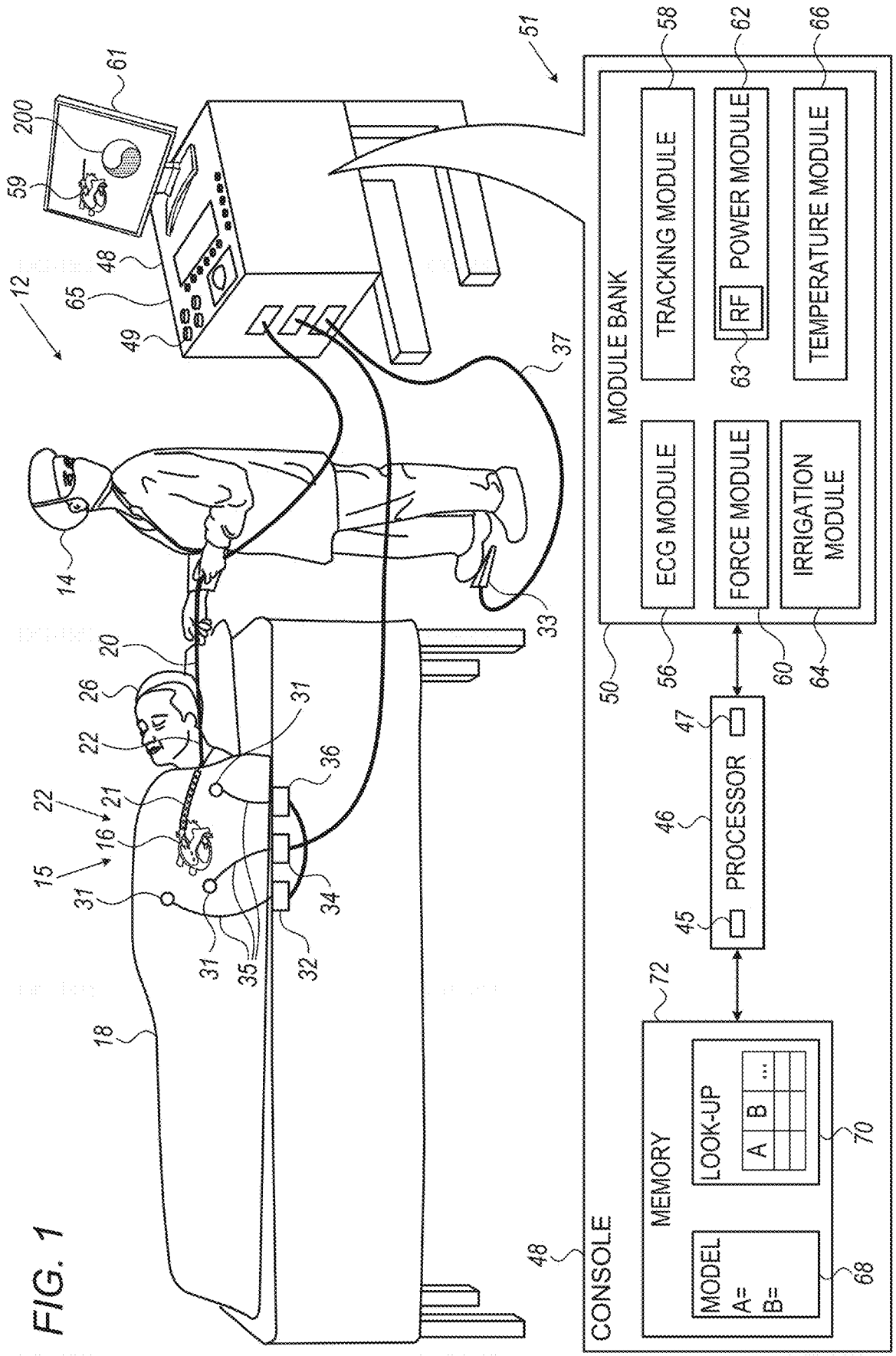
FIG. 1 is a schematic illustration of an invasive medical procedure using a cardiac ablation apparatus constructed and operative in accordance with an embodiment of the present invention.

An ablation procedure using a focal catheter may require multiple individual ablations, for example, but not limited to, ablating along a line of tissue. For such a procedure, a physician typically positions the catheter at an initial region of the tissue, and decides the parameters that should be used for that ablation (e.g., time, power to be applied, force, etc.). The physician then ablates that initial region and then moves the catheter to another region of the tissue and repeats the above operation including setting parameters. The physician repeats this process for as many regions in the tissue as required to form the ablation line. The process is time-consuming, and requires physician decision making before, during, and after each ablation regarding medical issues as well as control of the ablation apparatus.

The process may lead to errors due to the number of decisions that need to be taken. Additionally, time is generally of the essence in cardiac procedures.

Embodiments of the present invention provide an apparatus to perform a semi-automated serial ablation procedure which speeds up the ablation process and reduces human error. In particular, in some embodiments after setting initial parameters, the physician moves an ablation probe from ablation site to ablation site and ablation is performed automatically by the apparatus at each site.

The ablation probe may be inserted by the physician (optionally with the help of a robotic arm) into a chamber of a heart until the probe reaches the first ablation site. The physician then actuates commencement of the serial ablation procedure by providing a user input such as pressing a button or depressing a foot pedal. In one embodiment, the serial ablation procedure progresses as long as the physician has his/her foot on the pedal or a finger on the button. When the physician releases the pedal/button the procedure pauses or is aborted. In some embodiments, the commencement and completion of the ablation procedure are actuated by separate user selections.

At the first ablation site, the apparatus ensures that the probe is steady with respect to the heart and automatically computes a thickness of the tissue at the site. The apparatus then automatically computes an ablation duration at the first ablation site based on the computed tissue thickness. The apparatus may perform other checks, for example, safety and/or performance checks, described hereinbelow. Once the ablation has been automatically performed by the apparatus, the physician manually (or with the help of the robotic arm), moves the probe to the next ablation site. At this next ablation site, the apparatus ensures that the probe is steady with respect to the heart and automatically computes a thickness of the tissue at this site as well as performing other checks. The apparatus automatically assumes that when the probe is steady for a given period of time, a new ablation site has been reached. The tissue thickness is then used by the apparatus to automatically compute an ablation duration at this ablation site. The ablation at this site is then performed automatically by the apparatus. In some embodiments, the computation of the tissue thickness and the ablation duration may be performed after the ablation has commenced. The procedure is repeated for further ablation sites until the physician signals that the procedure is completed, e.g., releasing the foot pedal or button or by depressing the pedal or button a second time.

The serial ablation procedure generally includes three states, a standby state, an ablation state, and a waiting state. During the serial ablation procedure, a graphic user interface (GUI) displays relevant parameters to the physician during the three states.

At an initial standby state, during which the physician positions the probe, real-time impedance and temperature values at a distal end of the probe are shown on the GUI. Once the physician is satisfied that the probe is correctly positioned, the physician may begin the serial ablation procedure by performing a selection action, such as by depressing the pedal or button. At this point, irrigation fluid which is pumped through the distal end of the probe may be increased from its idle irrigation rate. Checking steps may also be performed such as checking whether the probe is steady and whether a force applied by the distal end of the probe on the tissue is within an acceptable range. The status of the irrigation rate may also be displayed on the GUI.

During approximately the first second of the ablation state, the apparatus estimates the thickness of the tissue being ablated and an ablation duration, for example using a method described in US Patent Publication 2018/0263690 of Govari, et al., which is herein incorporated by reference. Other methods may be used to estimate the thickness and the ablation duration. Similarly, the ablation duration may be computed using a method that is not based on thickness, such as based on the method described in US Patent Publication 2011/0152856 of Govari, et al., which is herein incorporated by reference. The estimated thickness and the total recommended ablation duration are displayed on the GUI and ablation at the first site commences. In some embodiments, the computation of the tissue thickness and the ablation duration may be performed after the ablation has commenced. During the ablation a change in impedance of the tissue is also displayed on the GUI. A time line may be shown on the GUI to show how much time has elapsed and/or remains for the ablation at this ablation site.

Once the ablation has finished, the procedure moves to a waiting state, where the apparatus waits, up to a preset time, for the physician to move the probe to a new site. A time-line may also be shown on the GUI to show when the waiting state expires. Expiry of the waiting state may lead to halting/pausing the serial ablation procedure, for example, by reverting the irrigation rate to the idle rate.

When the probe is at the new site, the apparatus may perform some checks such as whether the probe is steady, whether the force applied by the distal end of the probe on the tissue is within an acceptable range, whether the current ablation site is far enough away from the previous ablation site, and/or whether enough time has elapsed since the previous ablation. If the results of the checks are positive, the apparatus computes the tissue thickness and ablation duration at this new site, displays the estimated thickness and the total recommended ablation duration on the GUI, and ablation at this new site commences. In some embodiments, the computation of the tissue thickness and the ablation duration may be performed after the ablation has commenced.

The apparatus performs the ablation/waiting states as long as the procedure is active (e.g., the physician depresses the foot pedal/button) and so long as in the waiting state the probe is moved to an acceptable position prior to the expiry of the waiting state. The physician may halt the serial ablation procedure at any time by releasing the foot pedal/button or similar user selection action.

In some embodiments, the serial ablation procedure may require a large number of ablations in a given area or along one or more lines. The physician may mark planned ablation sites or one or more planned ablation lines or areas on a map of the myocardium. The physician guides the probe to one of the planned ablation sites, lines, or areas and signals the serial ablation procedure to begin. After further movement of the probe by the physician (in the area or along the line), ablation at subsequent ablation sites is performed automatically based on an identified proximity to another planned ablation site and/or based on a given distance from a previous ablation site.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Reference is now made to FIG. 1, which is a schematic illustration of an invasive medical procedure using an apparatus 12 according to an embodiment of the present invention. Reference is also made to FIG. 2, which is a schematic illustration of a distal end 22 of a probe 20 used in the apparatus 12 according to an embodiment of the present invention. The procedure is performed by a physician 14, and in the description hereinbelow the procedure is assumed to comprise an ablation of a portion of tissue 15 of a myocardium 16 of the heart of a human patient 18.

In order to perform the investigation, the physician 14 inserts the probe 20 into a sheath 21 that has been prepositioned in a lumen of the patient 18 so that the probe 20 is inserted into a chamber of the heart. The sheath 21 is positioned so that the distal end 22 of the probe 20 enters the heart of the patient 18. The distal end 22 comprises a position sensor 24 that enables the location and orientation of the distal end 22 to be tracked, a force sensor 26 that measures the force applied by the distal end 22 when it contacts the myocardium 16, and one or more temperature sensors 28 that measure the temperature at respective locations of the distal end 22. The distal end 22 also comprises an electrode 30 which is used to apply radiofrequency power to the myocardium 16 in the chamber so as to ablate the myocardium 16. The electrode 30 may also be used to acquire electropotentials from the myocardium 16, as noted below.

The apparatus 12 is controlled by a system processor 46, which is located in an operating console 48 of the apparatus. The operating console 48 comprises controls of at least one user input device 49 which are used by the physician 14 to communicate with the processor 46. A foot-pedal 33 connected to the operating console 48 via a cable 37 (or a wireless connection) may be used by the physician 14 as an input device. The software for processor 46 may be downloaded to the processor 46 in electronic form, over a network, for example. Alternatively, or additionally, the software may be provided on non-transitory tangible media, such as optical, magnetic, or electronic storage media.

The processor 46 comprises real-time noise reduction circuitry 45, typically configured as a field programmable gate array (FPGA), followed by an analog-to-digital (A/D) signal conversion integrated circuit 47. The processor 46 can pass the signal from the A/D signal conversion integrated circuit 47 to another processor and/or can be programmed to perform at least one algorithm disclosed herein, the algorithm comprising steps described hereinbelow. The processor 46 uses the noise reduction circuitry 45 and the A/D signal conversion integrated circuit 47, as well as features of modules which are described in more detail below, in order to perform the algorithm.

In order to operate the apparatus 12, the algorithm of the processor 46 communicates with a module bank 50, which has a number of modules used by the processor to operate the apparatus 12. Thus, the module bank 50 comprises an electrocardiograph (ECG) module 56 which acquires and analyzes signals from the electrode 30, and a tracking module 58 which receives and analyzes signals from the position sensor 24, and which uses the signal analysis to generate a location and an orientation of the distal end 22. In some embodiments the position sensor 24 comprises one or more coils which provide the sensor signals in response to magnetic fields traversing the coils. In these embodiments, in addition to receiving and analyzing signals from sensor 24, tracking module 58 also controls radiators 32, 34, and 36 which radiate the magnetic fields traversing the position sensor 24. The radiators 32, 34, 36 are positioned in proximity to the myocardium 16, and are configured to radiate alternating magnetic fields into a region in proximity to the myocardium 16. A plurality of wire connections 35 link the operating console 48 with body surface electrodes 31 and other components (such as the radiators 32, 34, 36 and the sensor 24) to enable the tracking module 58 to measure location and orientation coordinates of the probe 20. In some embodiments, the tracking module 58 is configured to compute a relative location and a relative orientation of the probe 20 with respect to the heart. Magnetic location and orientation tracking is described in U.S. Pat. Nos. 7,756,576 and 7,536,218, which are hereby incorporated by reference. The Carto® system produced by Biosense Webster, of 33 Technology Drive, Irvine, Calif. 92618 USA, uses such a magnetic tracking system. The tracking module 58 is not limited to using magnetic based location and orientation tracking. Any suitable location and orientation tracking can be used, such as impedance-based or image-based tracking.

The apparatus 12 may receive image data from an external imaging modality, such as an MRI unit, CT unit or the like and includes image processors that can be incorporated in or invoked by the processor 46 for generating and displaying images. The image data may be registered with the tracking module 58 and an image 59 combining the received data and positions of the probe 20 may be displayed to the physician 14 on a display 61. For example, the track of the distal end 22 of the probe 20 may be shown on a three-dimensional representation of the heart of patient 18 that is displayed on the display 61. A user interface screen 200 may also be displayed on the display 61 for tracking the status of an ablation procedure, for example a serial ablation procedure. The user input device 49 and the display 61 are herein termed a user interface providing an interface between the physician 14 and the elements of the operating console 48.

The electrode 30 and the body surface electrodes 31 may be used to measure tissue impedance at the ablation site as taught in U.S. Pat. No. 7,536,218, issued to Govari et al., which is herein incorporated by reference.

The module bank 50 also comprises a force module 60, a power module 62, an irrigation module 64, and a temperature module 66. The functions of these modules are explained below. The modules in the module bank 50, and the processor 46, are herein termed processing circuitry 51.

The force module 60 receives signals from the force sensor 26, and from the signals generates a magnitude CF of the contact force, herein assumed to be measured in grams, exerted by the distal end 22 on the tissue 15. In some embodiments the force sensor 26 is configured so that the signals it provides to the force module 60 enable the force module 60 to evaluate a direction of the force exerted by the distal end 22 on the tissue 15.

The power module 62 comprises a radiofrequency (RF) signal generator 63 which generates the radiofrequency power to be applied by the electrode 30 to ablate the tissue 15 of the myocardium 16. The processor 46 and the power module 62 are able to adjust a power level P, herein assumed to be measured in Watts, delivered by the electrode 30, as well as a length of time t, measured in seconds, during which the power is delivered, as described in more detail below.

The irrigation module 64 controls a rate of flow V, herein assumed to be measured in mL/min, of irrigation fluid, typically normal saline solution, supplied to the distal end 22 by a pump 65 disposed in the operating console 48. The probe 20 includes an irrigation channel through which to irrigate the myocardium 16. The irrigation fluid is expelled from irrigation holes 80 in the distal end 22. The pump 65 is configured to selectively pump the irrigation fluid into the irrigation channel at an idle rate and at one or more one non-idle rates (higher than the idle rate) according to a status of the ablation procedure.

The temperature module 66 receives a temperature signal provided the temperature sensor 28 (or by each temperature sensor 28). The temperature signal is indicative of a temperature of the myocardium at a plurality of different times. The temperature module 66 determines the temperatures registered by each of the sensors 28. Typically, in the case of multiple sensors 28 the temperature module 66 determines a mean temperature T of the distal end 22. Additionally, in the case of multiple sensors, the temperature module 66 may produce a map of the temperature distribution of the distal end 22.

US Patent Publication 2018/0263690 of Govari, et al., mentioned above, describes that on injection of a heat energy pulse into tissue 15 an overall thickness D of the tissue 15 affects the rate of change of temperature $$\frac{\Delta T}{\Delta t}$$

measured by one or more of the temperature sensors 28. In particular, for a given irrigation rate V of fluid through the distal end 22, and for a given contact force CF applied to the tissue 15 by the distal end 22, the rate of change of temperature $$\frac{\Delta T}{\Delta t}$$

is large for large values of D and is small for small values of D, i.e., the rate of change of temperature increases as the thickness D increases. The heat energy pulse may be injected into the tissue 15 by applying a radiofrequency energy pulse for a short time to the tissue 15. The inventors of the US Patent Publication 2018/0263690 believe that the relationship described above, between the rate of change of temperature $$\frac{\Delta T}{\Delta t}$$

and the overall tissue thickness D, is due to the heat energy retained by the tissue 15. I.e., tissue having a large D retains more heat energy than tissue having a small D.

The relationship may be expressed by the following equation (1):

$$D = f\left(\frac{\Delta T}{\Delta t}\right) \tag{1}$$

where D is the thickness of the tissue 15,
ΔT is the change of temperature of the distal end 22 in a time period Δt, and
f is a function.

In one embodiment, the function f is as given in equation (2) below:

$$D = A\left(1 - e^{-\frac{s}{B}}\right)^n \tag{2}$$

where n is a numerical exponent, and A, B are constant parameters having values which depend on the thermal characteristics of the distal end 22 of the probe 20, and s is a normalized slope of a temperature-time graph, i.e., $$S = \left[\frac{\Delta T}{\Delta t}\right]_{NORM} \tag{2a}$$

The non-normalized slope of the temperature-time graph, $$\frac{\Delta T}{\Delta t},$$

depends on the contact force CF applied by the distal end 22 to the tissue 15, the level P of the radiofrequency pulse power applied, the length of time t of application of the radiofrequency power pulse, and the irrigation rate V.

The non-normalized slope, $$\frac{\Delta T}{\Delta t},$$

is converted to a normalized slope, $$\left[\frac{\Delta T}{\Delta t}\right]_{NORM},$$

by normalizing CF to a normalized contact force $CF_{NORM}$, P to a normalized pulse power $P_{NORM}$, t to a normalized a pulse length $t_{NORM}$, and V to a normalized irrigation rate $V_{NORM}$. The normalization assumes respective relationships between the non-normalized slope and the contact force CF, the P pulse power P applied, the pulse length t, and the irrigation rate V. In an embodiment the relationships for CF, P, and t are assumed to comprise respective direct proportionalities, and the relationship for V is assumed to comprise an inverse proportionality. However, other relationships, that may be used in normalizing the slope of the temperature-time graph, will be apparent to those having ordinary skill in the art, and all such relationships are assumed to be comprised within the scope of the present invention.

In an embodiment, the numerical exponent n in equation (2) is set as 1 or 2. In other embodiments the value for n may be set to be different from 1 and 2, and may be a non-integer value.

Values of A and B, as well as the normalized values referred to above, and values of the parameters of the relationships for normalizing the slope $$\frac{\Delta T}{\Delta t},$$

may be stored as a model 68 and/or in a look-up table 70 contained in a memory 72 that is accessed by the processor 46.

Reference is now made to FIG. 3, which is a graph of tissue thickness against a normalized rate of temperature change at the distal end 22 of the probe 20 of FIG. 2. FIG. 3 is a schematic graph of D vs. s, as determined from equation (2), for n=1, according to an embodiment of the present invention. As is illustrated in the graph, the slope s, $$\left[\frac{\Delta T}{\Delta t}\right]_{NORM},$$

i.e., the normalized rate of temperature change, increases monotonically with respect to the tissue thickness D. As is also illustrated, the graph exponentially approaches an asymptote D=A as the slope s increases, and for a normalized rate of temperature change of B, the thickness D is equal to 0.63 A.

For clarity and simplicity, except where otherwise stated, the following description assumes that the relationship between the tissue thickness and the rate of change of temperature is as given by equation (2) with n=1. Those having ordinary skill in the art will be able to modify the description, mutatis mutandis, for other values of n and for other relationships of the form of equation (1).

Prior to performing an actual ablation procedure, the physician 14 may determine values for A and B in equation (2), as well as values for the relationships used for normalizing the slope $$\frac{\Delta T}{\Delta t},$$

by ablation of tissue using measured values of tissue thickness D and slope $$\frac{\Delta T}{\Delta t}.$$

Typically, such a determination involves using a range of values of irrigation rate V, radiofrequency pulse power P, length of time t of the pulse, and contact force CF. The values of P, V, and t are typically chosen so that the temperature of the tissue being used remains within a range of approximately 40° C.-60° C., so that any change of temperature is not harmful to the tissue.

In one embodiment the values for V are set within a range 10-20 mL/min, the values of P are set within a range of 20-30 W, the pulse length t is set within a range of 1-3 s, the contact force CF is within a range of 5-25 grams, and the normalized values are set at $V_{NORM}$=15 mL/min, $P_{NORM}$=25 W, $t_{NORM}$=2 s, and $CF_{NORM}$=15 grams. However, providing that the temperature of the tissue being used remains between approximately 40° C.-60° C., V, P, and t may have values outside these ranges, and the normalized values may be different from those provided here, and such alternative values may be determined by one with ordinary skill in the art without undue experimentation.

To determine A and B for a catheter, a distal end of the catheter is brought into contact with tissue of a known thickness D, and the distal end is configured to exert the normalized contact force $CF_{NORM}$ on the tissue while the distal end and tissue are irrigated at the normalized irrigation rate $V_{NORM}$. A radiofrequency pulse with the normalized power $P_{NORM}$ and pulse length $t_{NORM}$ is applied to the tissue, and the temperature T of the distal end is recorded as it changes over time. From the recordation of the distal end temperatures and times, an estimate of the normalized slope, $$\left[\frac{\Delta T}{\Delta t}\right]_{NORM},$$

is made. In one embodiment, the value of $$\left[\frac{\Delta T}{\Delta t}\right]_{NORM}$$

is calculated from the change of temperature ΔT for a value of Δt of 5 s, where the value Δt is taken over the first 5 s of recordation.

The above determination is repeated for different values of tissue thickness D, giving respective different values of $$\left[\frac{\Delta T}{\Delta t}\right]_{NORM},$$

to get A and B values for the catheter.

For each selected catheter/probe, the physician 14 may use the processor 46 to store the respective values of A, B, as mathematical model 68 (FIG. 1). The model 68 is a mathematical function, such as a cost function, that enables the processor 46 to determine values of A and B from the experimental values of V, P, t and CF, together with values for the respective normalizing relationships to the normalized values $V_{NORM}$, $P_{NORM}$, $t_{NORM}$ and $CF_{NORM}$, as described above. Alternatively, or additionally, physician 14 may configure the processor 46 to store the respective values of A and B for each selected catheter/probe, as well as the values for the respective relationships in the look-up table 70.

Figure 4:
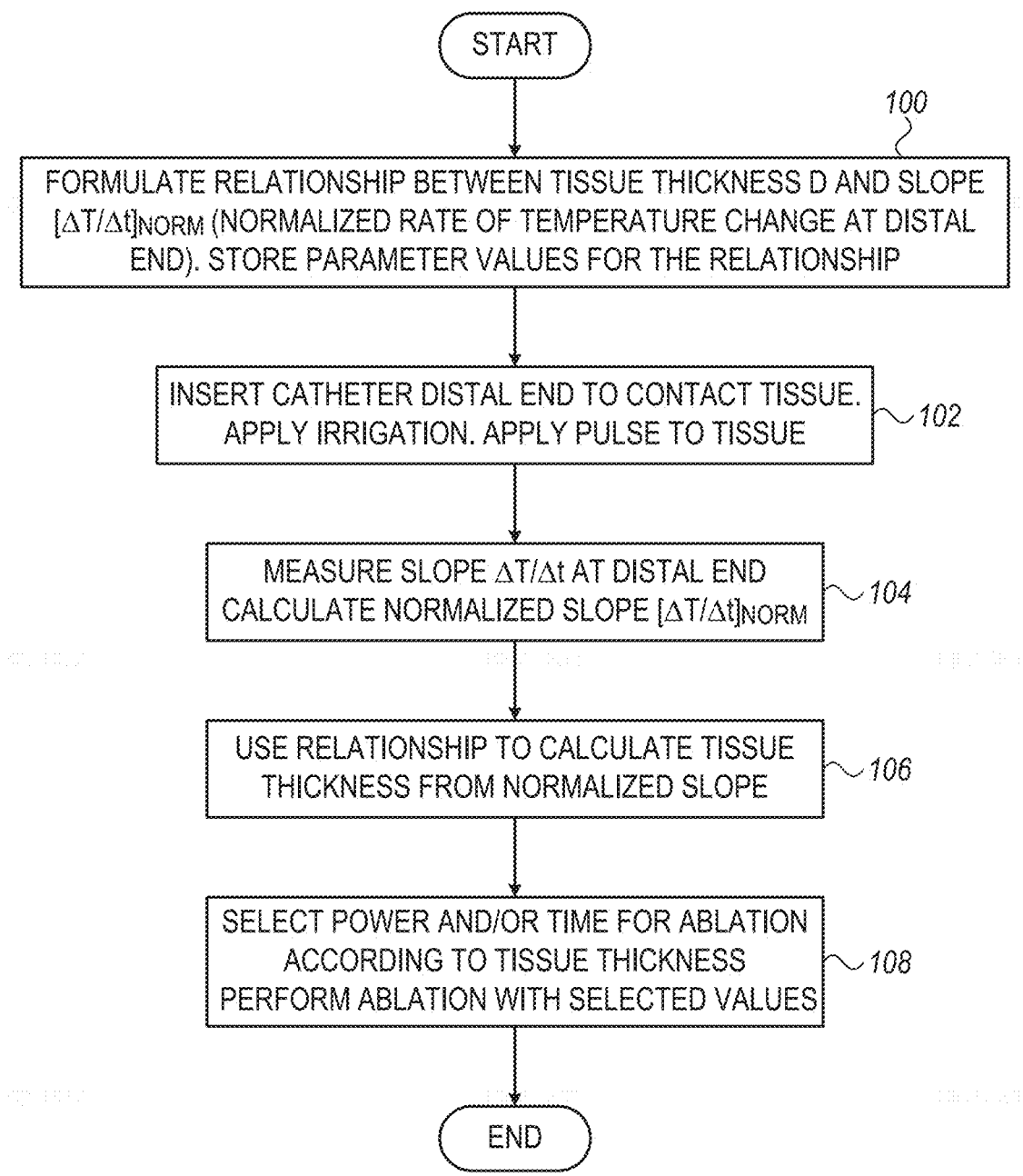
FIG. 4 is a flow chart including exemplary steps in a method of computing tissue thickness and ablation duration in the apparatus of FIG. 1.

Reference is now made to FIG. 4, which is a flow chart including exemplary steps in a method of computing tissue thickness and ablation duration in the apparatus 12 of FIG. 1. Although FIG. 4 generally describes computing an ablation duration for a single ablation site, FIG. 4 may be used to compute ablation durations for different respective ablation sites for use in the serial ablation procedure described in more detail with reference to FIGS. 5-10.

In a preparatory step 100 that is typically performed before the start of an ablation procedure, the relationship between tissue thickness D and normalized slope s, i.e., the normalized rate of temperature change $$\left[\frac{\Delta T}{\Delta t}\right]_{NORM}$$

of distal end 22, is formulated. As stated above, for simplicity and clarity the relationship herein is assumed to correspond to equation (2) with n=1. In addition to formulating the relationship, in step 100 values for parameters of the relationship, in this case A and B, as well as parameters for the normalizing relationships are stored as look-up table 70 and/or mathematical model 68, as described above. Typically, a catheter having a distal end similar to the distal end 22 that is used in the ablation procedure of the present flowchart is used to perform the evaluations and/or generate look-up table 70 and mathematical model 68.

In an initial procedure step 102, the physician 14 inserts the distal end 22 to contact a selected portion of the tissue 15 of the myocardium 16, and the force module 60 and processor 46 record a contact force CF sensed by the force sensor 26. Once in contact with the tissue 15, the physician 14 sets a flow rate V of irrigation to the distal end 22. In some embodiments, the flow rate may be set automatically by the irrigation module 64. Typically, the value for V is set within a range 10-20 mL/min, but V may have a value outside this range. In addition, while the distal end 22 and the tissue 15 are being irrigated, the processor 46 uses the electrode 30 to apply a radiofrequency power pulse to the tissue 15 in contact with the distal end 22. In one embodiment the processor 46 sets the pulse to have a power P of 30 Watts and a duration t of 1 second. The processor 46 records the values of V, P, and t.

In a slope measurement step 104, once the pulse has been applied to the tissue 15, the processor 46 begins recording the temperature of one or more of the temperature sensors 28, as well as the times of recordation. From the temperatures and the times, the processor 46 evaluates a value of the slope $$\frac{\Delta T}{\Delta t}.$$

From the slope, the processor 46 calculates the normalized rate of temperature change $$\left[\frac{\Delta T}{\Delta t}\right]_{NORM},$$

i.e., the normalized slope of the corresponding temperature-time graph, of the distal end 22.

In a tissue thickness step 106, the processor 46 applies the normalized slope found in step 104 to the relationship formulated in step 100, together with appropriate values for parameters A, B, of the relationship, to evaluate a thickness D of tissue 15. For the relationship corresponding to equation (2) with n=1, the values of A and B are found from look-up table 70 and/or mathematical model 68.

In an ablation step 108, the processor 46 uses the evaluated tissue thickness D to estimate a radiofrequency power P and a duration time t for which the power is to be applied, to ablate tissue 15. The estimation typically uses an ablation index, described below.

As is known in the art, an ablation index is a function, having a value that changes as ablation proceeds, which provides an estimate of the size of a lesion produced by the ablation of a tissue of known type. The estimate provided by the index depends on the values of the contact force CF and power P measured during the ablation, as well as on the period of time of the ablation. Ablation indices are described in an article entitled "Ablation Index-guided Pulmonary Vein Isolation for Atrial Fibrillation may Improve Clinical Outcomes in Comparison to Contact Force-guided Ablation" to Hussein et al., presented at the 2016 Heart Rhythm Congress, and in U.S. Patent Application 2017/0014181 to Bar-Tal et al. Both documents are incorporated herein by reference.

Equation (3) below gives an expression for an ablation index:

$$D = (C \int_0^t CF^\alpha(\tau) P^\beta(\tau) d\tau)^\delta \equiv \text{Ablation Index} \quad (3)$$

where C is a constant having a value depending on the type of tissue being ablated; in one embodiment C has an approximate value of 0.002, α is an exponent having a value typically in the range 0.6-0.8, β is an exponent having a value typically in the range 1.4-1.8, δ is an exponent having an approximate value of 0.35, and D is an estimate of the depth of a lesion achieved by ablating for a time t, with instantaneous contact force $CF(\tau)$ and instantaneous power $P(\tau)$, and where τ represents a time variable.

If the contact force and the power are assumed to be constant, having respective values $\overline{CF}$ and $\overline{P}$ during an ablation procedure that is to take a time t, then equation (3) may be rewritten as equation (4):

$$D = (C \, \overline{CF}^\alpha \overline{P}^\beta t)^\delta \quad (4)$$

The value of the left side of equation (4), tissue thickness D, is known from step 106. Processor 46 may thus use the right side of equation (4) to provide to physician 14 recommended values of power P and time t for ablation using the measured value of force CF and an estimate of C.

In step 108 physician 14 selects one of the recommended values of power P and time t to ablate tissue 15, and concludes the ablation of tissue 15 with these values.

The description above of steps of the flowchart assumes that physician 14 uses an ablation index in determining values of power to be applied during an ablation procedure. The ablation index acts as an aid to the physician in deciding values of parameters, such as power and time period of ablation, to be used during an ablation procedure. However, it will be understood that the physician may not use an ablation index in deciding values of such parameters, while still using the description of tissue thickness step 106 to estimate the thickness of tissue being ablated, and may adapt the flowchart description, mutatis mutandis, for such a case. It will thus be understood that the scope of the present invention includes cases where an ablation index is not used. For example, the physician 14 may select or enter a value of the power to be applied and the apparatus 12 may compute the ablation duration accordingly.

The description above has also assumed that the rate of change of temperature of the catheter distal end, i.e., the slope of the temperature-time graph, is normalized. Nevertheless, those having ordinary skill in the art will be able to adapt the description to accommodate cases where the rate of change of temperature of the catheter distal end is not normalized.

Figure 5:
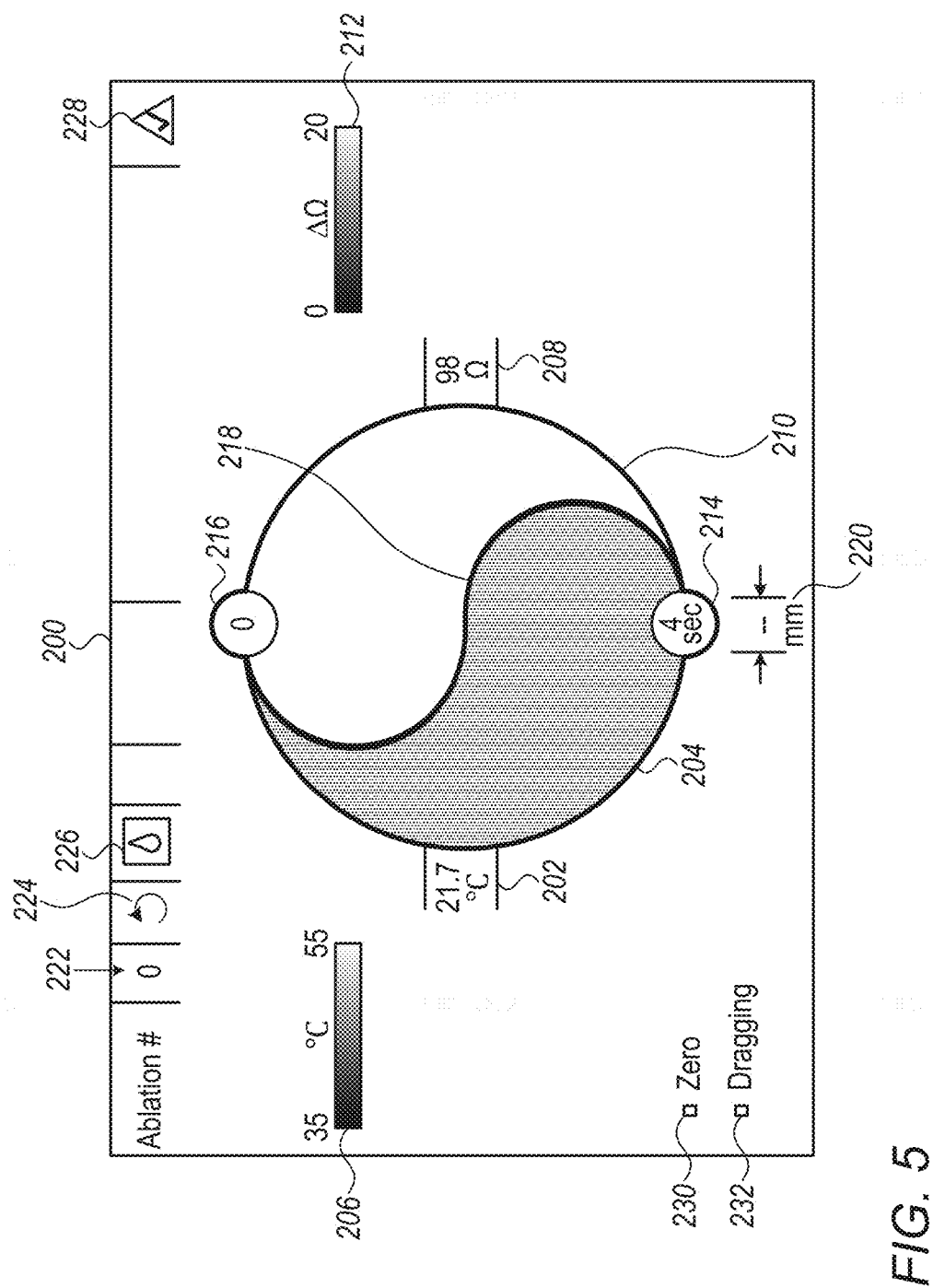
FIG. 5 is a user interface screen describing a standby state prior to a serial ablation procedure in the apparatus of FIG. 1.

Reference is now made to FIG. 5, which is the user interface screen 200 describing a standby state in the apparatus 12 of FIG. 1. Reference is also made to FIGS. 1 and 2. The user interface screen 200 includes a plurality of indicators such as a temperature indicator 202 numerically indicating the temperature at the distal end 22 of the probe 20 (e.g., indicative of a temperature of the myocardium 16), a colored area 204 having a color indicative of the temperature at the distal end 22 (e.g., indicative of a temperature of the myocardium 16), a color coded legend 206 providing a look-up to estimate a temperature indicated by the color of the colored area 204, an impedance indicator 208 numerically indicating the impendence measured by the probe 20 (e.g., indicative of an impedance of the myocardium 16), a colored area 210 having a color indicative of an impedance measurement measured by the probe 20 (e.g., indicative of an impedance of the myocardium 16), and a color coded legend 212 providing a look-up to estimate an impedance indicated by the color of the colored area 210. In the standby state, prior to performing any ablations, and in a waiting-state described in more detail with reference to FIG. 7, the impedance indicator 208 and the colored area 210 indicate impedance. In the ablation state, while ablation is being performed, the impedance indicator 208 and the colored area 210 indicate a change in impedance caused by ablation at the ablation site.

The user interface screen 200 also includes a time indicator 214. After the probe 20 has been inserted by the physician 14 to the first ablation site, the physician 14 signals commencement of the serial ablation procedure, for example, by the physician 14 depressing the foot pedal. The time indicator 214 may indicate an estimated preparation time until the apparatus 12 will be ready to perform ablation, for example, an estimated time for increasing the irrigation rate from an idle rate to a non-idle rate. The user interface screen 200 also includes a moving time indicator 216 which moves along a line 218 and is indicative of the time-elapsed (and time remaining) during the preparation time period. As the moving time indicator 216 moves along the line 218, the value inside the moving time indicator 216 is updated to reflect how much time has elapsed during the preparation time period. The user interface screen 200 also includes an indicator 220 of the thickness of the myocardium 16. In the standby state the indicator 220 does not indicate a thickness value. The user interface screen 200 also includes an ablation number 222 (which is now equal to zero prior to commencement of ablation) in the serial ablation procedure. The user interface screen 200 also includes a reset button 224 (to reset the ablation number 222 to zero at the beginning of a new procedure), an irrigation rate symbol 226 indicating a level of the irrigation rate being provided, a system ready symbol 228 indicating that the various hardware elements (e.g. probes and sensors) are operational, and if required, are connected to the operating console 48, a zero selector 230 (for the physician 14 to enter parameters such as target power, target temperature etc., prior to commencing the serial ablation procedure), and a dragging selector for the physician 14 to select whether the apparatus 12 is operating in single ablation site mode or serial ablation procedure mode.

Prior to ablation other checks may be performed, for example, checking if the force applied by the distal end 22 is within an acceptable range. The various checks are described in more detail with reference to FIG. 10.

Figure 6:
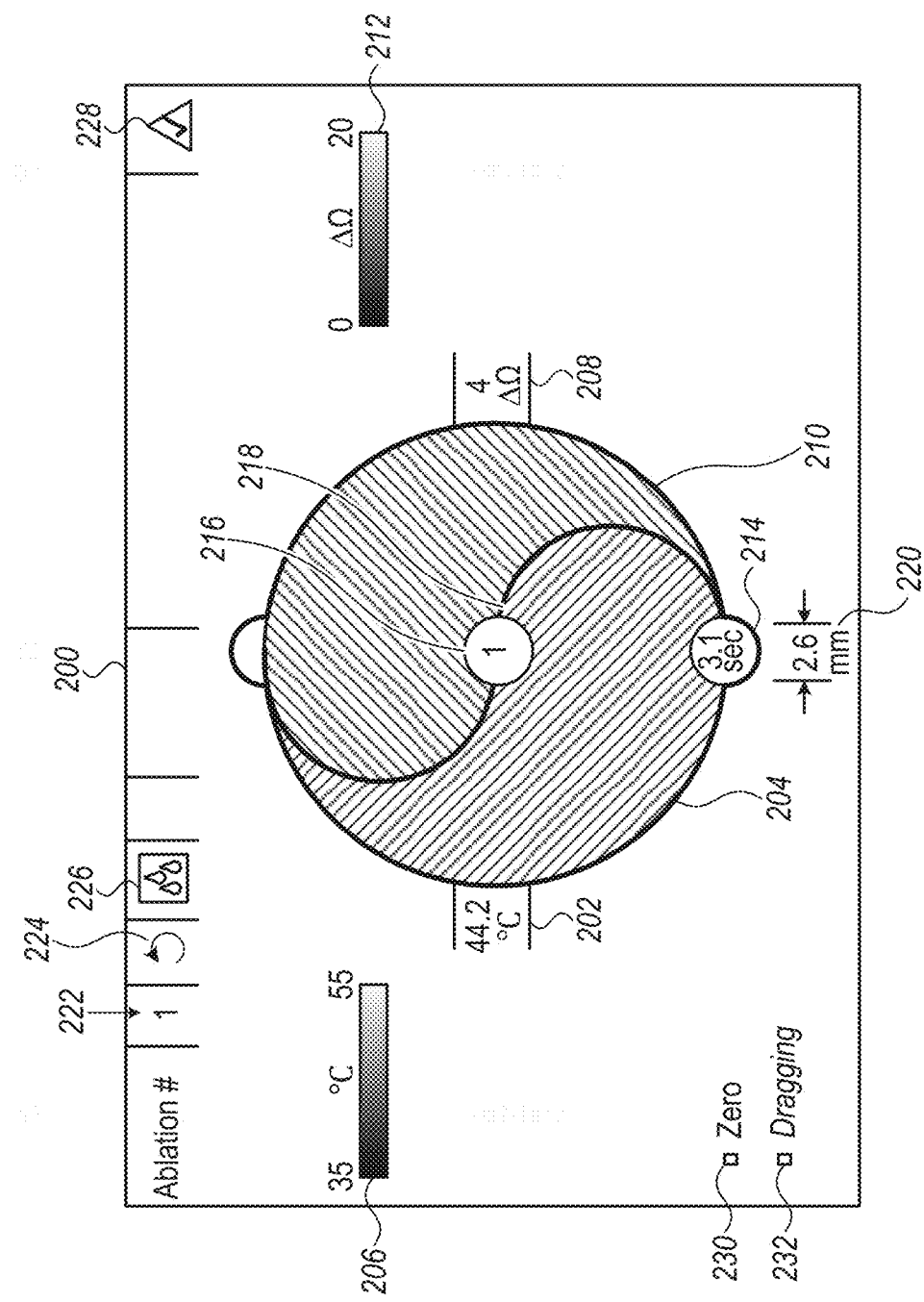
FIG. 6 is a user interface screen describing an active ablation state in the serial ablation procedure operated by the apparatus of FIG. 1.

Reference is now made to FIG. 6, which is the user interface screen 200 describing an active ablation state in the serial ablation procedure operated by the apparatus 12 of FIG. 1. Prior to ablation, the tissue thickness and the ablation duration are computed at the ablation site. The tissue thickness is shown by the indicator 220 and the ablation duration is shown by the time indicator 214. In some embodiments, the computation of the tissue thickness and the ablation duration may be performed after the ablation has commenced. As the ablation progresses, the moving time indicator 216 moves along the line 218 showing the time elapsed during the ablation and/or the time remaining until the end of the ablation. The value in the moving time indicator 216 is updated as the elapsed time increases. The impedance indicator 208 and the colored area 210 indicate the change in impedance of the myocardium 16 caused by the ablation and are updated during the ablation. The ablation number 222 now shows number 1 and the irrigation rate symbol 226 shows that the irrigation rate is at a non-idle rate. Once the ablation is completed, the serial ablation procedure moves to a waiting state described below with reference to FIG. 7.

Figure 7:
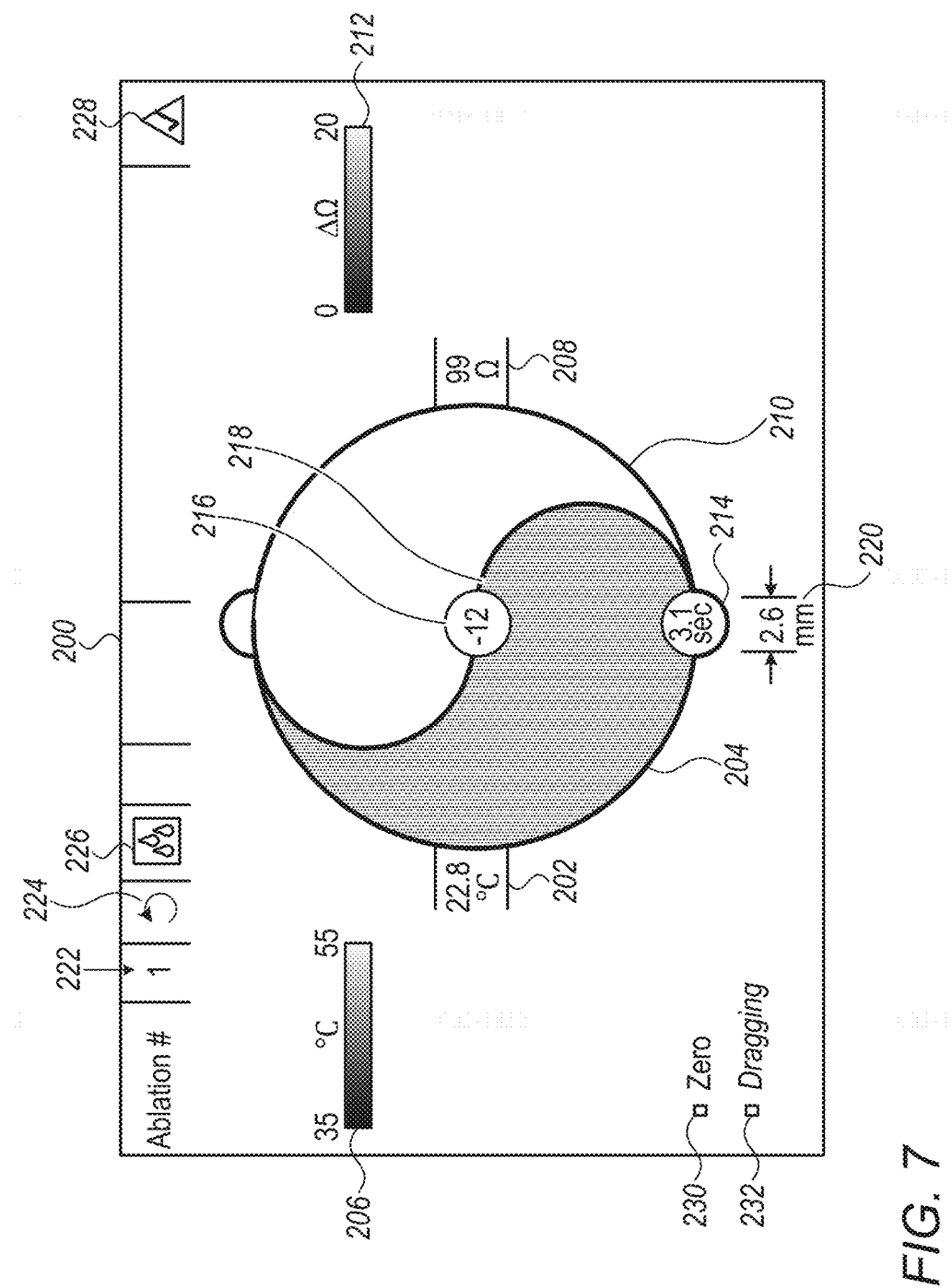
FIG. 7 is a user interface screen describing a waiting state in the serial ablation procedure operated by the apparatus of FIG. 1.

Reference is now made to FIG. 7, which is the user interface screen 200 describing a waiting state in the serial ablation procedure operated by the apparatus of FIG. 1. In the waiting state, the ablation number 222, the indicator 220 and the time indicator 214 are generally not updated. In some embodiments, the time indicator 214 may be updated to reflect a maximum length of the waiting state (waiting time period) before the serial ablation procedure is automatically halted. The moving time indicator 216 moves along the line 218 in the waiting state indicating a time elapsed (remaining) in the waiting state. The value in the moving time indicator 216 may also be updated to reflect the time elapsed/remaining during the waiting state. If the probe 20 is moved to the next ablation site during the waiting state, the waiting state transitions to a new ablation state in the serial ablation procedure.

Figure 8:
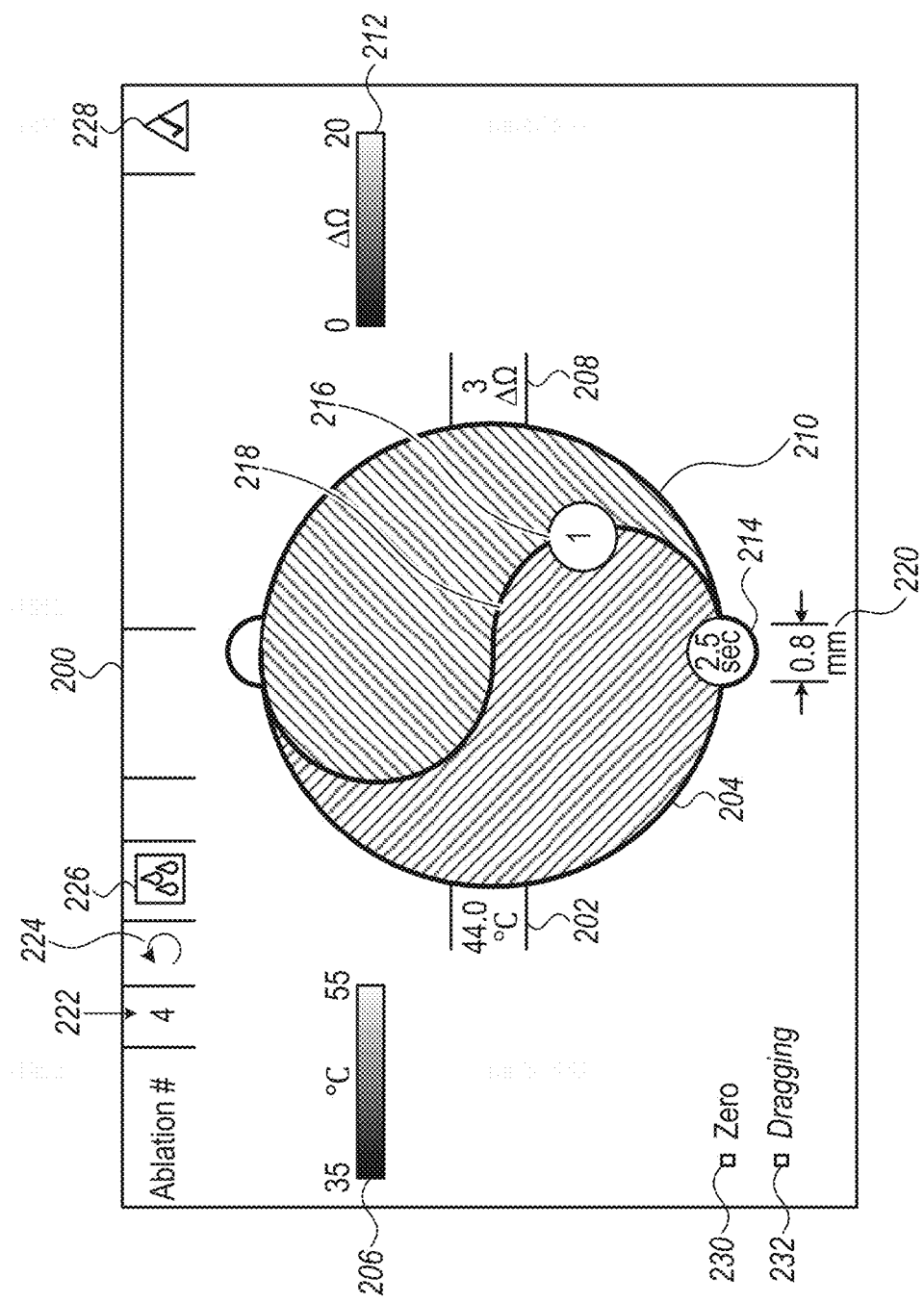
FIG. 8 is a user interface screen describing an additional active ablation state in a serial ablation procedure operated by the apparatus of FIG. 1.

Reference is now made to FIG. 8, which is the user interface screen 200 describing an additional active ablation state in the serial ablation procedure operated by the apparatus 12 of FIG. 1. FIG. 8 shows a 4$^{th}$ ablation state in the serial ablation procedure at an ablation site with a tissue thickness of 0.8 mm and a computed ablation duration of 2.5 seconds associated with the tissue thickness of 0.8 mm. The serial ablation procedure moves from ablation state to waiting state and cycles between these two states as long as the serial ablation procedure is signaled as being active by the physician 14.

Figure 9:
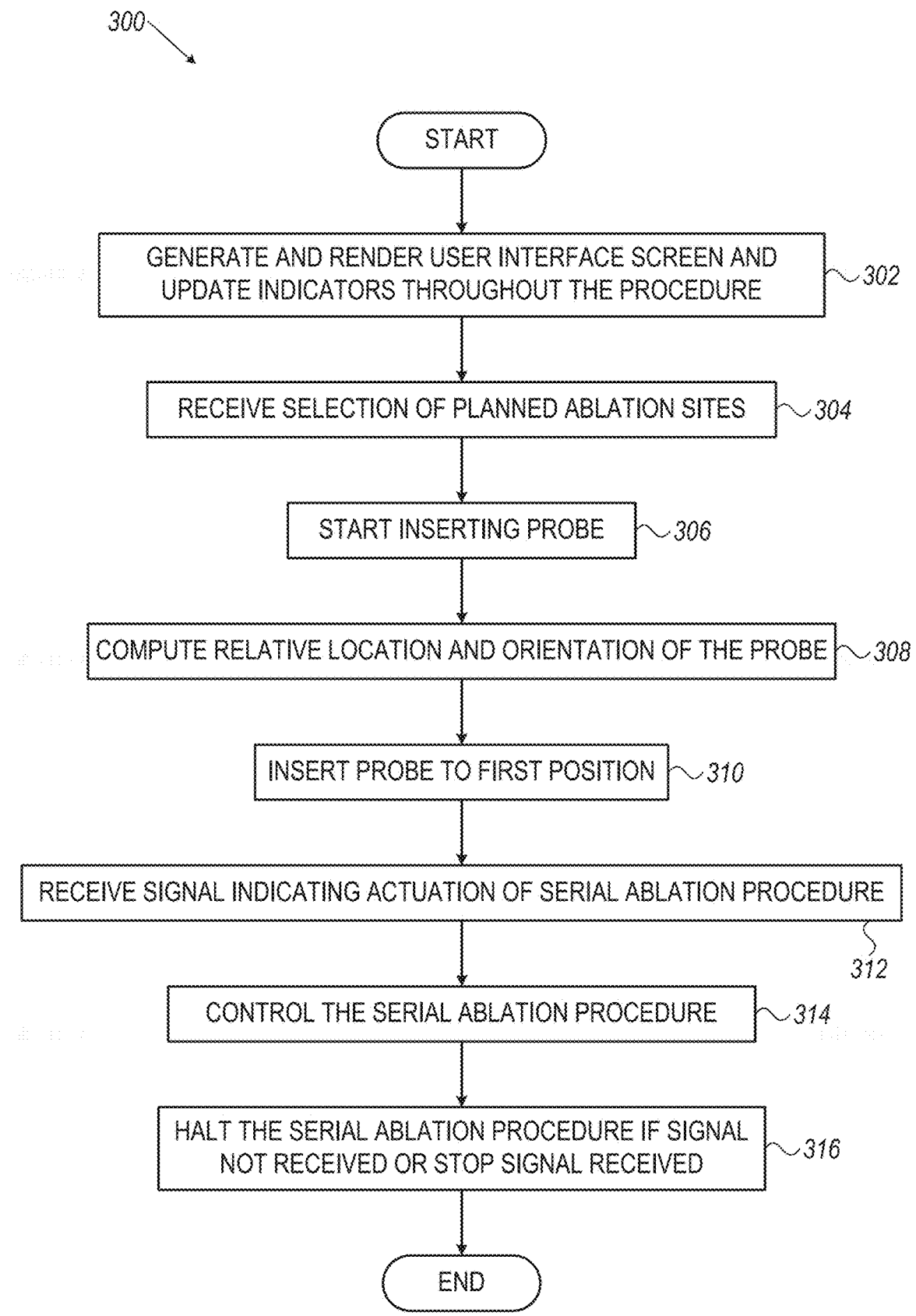
FIG. 9 is a flow chart including exemplary steps in a method of performing the serial ablation procedure in the apparatus of FIG. 1.

Reference is now made to FIG. 9, which is a flow chart 300 including exemplary steps in a method of performing the serial ablation procedure in the apparatus 12 of FIG. 1. Reference is also made to FIGS. 1, 2 and 5. The order of the steps shown in FIG. 9 is provided by way of example only. The steps may be performed in any suitable order including performing more than one step at the same time.

The processor 46 is configured to render (block 302), to the display 61, the user interface screen 200 including a plurality of indicators describing a state of the serial ablation procedure. The indicators may include the time indicator 214 (indicating the ablation duration or preparation time period in the standby state or the waiting time in the waiting state) and the moving time indicator 216 indicating a time elapsed or remaining (e.g., until an end of the ablation duration at the relative location, or an end of the preparation time period in the standby state, or an end of the waiting time in the waiting state). The indicators may also include a temperature (of the myocardium 16 or region surrounding the probe 20) using the temperature indicator 202 and the colored area 204. The indicators may include an impedance measured by the probe 20 or a change of impedance of the myocardium 16 during ablation using the impedance indicator 208 and the colored area 210. The indicators may also include the indicator 220 indicating a thickness of the myocardium 16, the irrigation rate symbol 226, the ablation number 222 in the serial ablation procedure, and any other suitable symbol or value including the symbols and values described above with reference to FIGS. 5-8. The various indicators shown in the user interface screen 200 are updated throughout the serial ablation procedure as described above with reference to FIGS. 5-8 and below with reference to FIG. 10.

In some embodiments, the serial ablation procedure may require a large number of ablations in a given area(s) or along one or more lines. The physician may mark planned ablation sites or one or more planned ablation lines or areas on a map of the myocardium. In some embodiments, the processor 46 is configured to receive (block 304) a signal from the user input device(s) 49 indicating selection of planned ablation sites and/or planned ablation area(s) and/or planned ablation line(s) having respective locations on a map of the myocardium 16. The physician 14 may mark planned ablation sites, line(s), or area(s) on the image 59 using a suitable pointing device or stylus.

The physician 14 starts inserting (block 306) probe 20. The physician 14 may be guided using the image 59 (FIG. 1). In some embodiments, the probe 20 may be held by a robotic arm to aid the physician 14 in the insertion process. During the insertion process, and throughout the procedure, the processor 46 is configured to compute (block 308) the relative location and orientation of the probe 20 with respect to the heart. The physician 14 inserts (block 310) the probe 20 to the first ablation position and then provides a user selection to start the serial ablation procedure, for example, by depressing the foot-pedal 33 or the user input device(s) 49. In some embodiments, the serial ablation procedure is only active while the foot-pedal 33 or the user input device(s) 49 is depressed/actively selected. In other embodiments, the serial ablation procedure is active until a second user selection is performed using the foot-pedal 33 or the user input device(s) 49.

The processor 46 is configured to receive (block 312) a signal from the user input device(s) (e.g. the foot-pedal 33 or the user input device(s) 49) indicating an actuation of the serial ablation procedure including performing a plurality of ablations over time at different locations of the myocardium 16. The processor 46 is configured to control (block 314) the serial ablation procedure responsively to receiving the signal so that for each ablation the processor 46 is configured to perform some or all of the steps included in the flow chart of FIG. 10, which describes the step of block 314 in more detail.

The processor 46 is configured to halt (block 316) the serial ablation procedure responsively to: (a) not receiving the signal from the user input device(s) (e.g., the physician 14 takes his foot of the foot-pedal 33 or releases a button of the user input device(s) 49); or (b) if a stop signal is received from the user input device(s).

Figure 10:
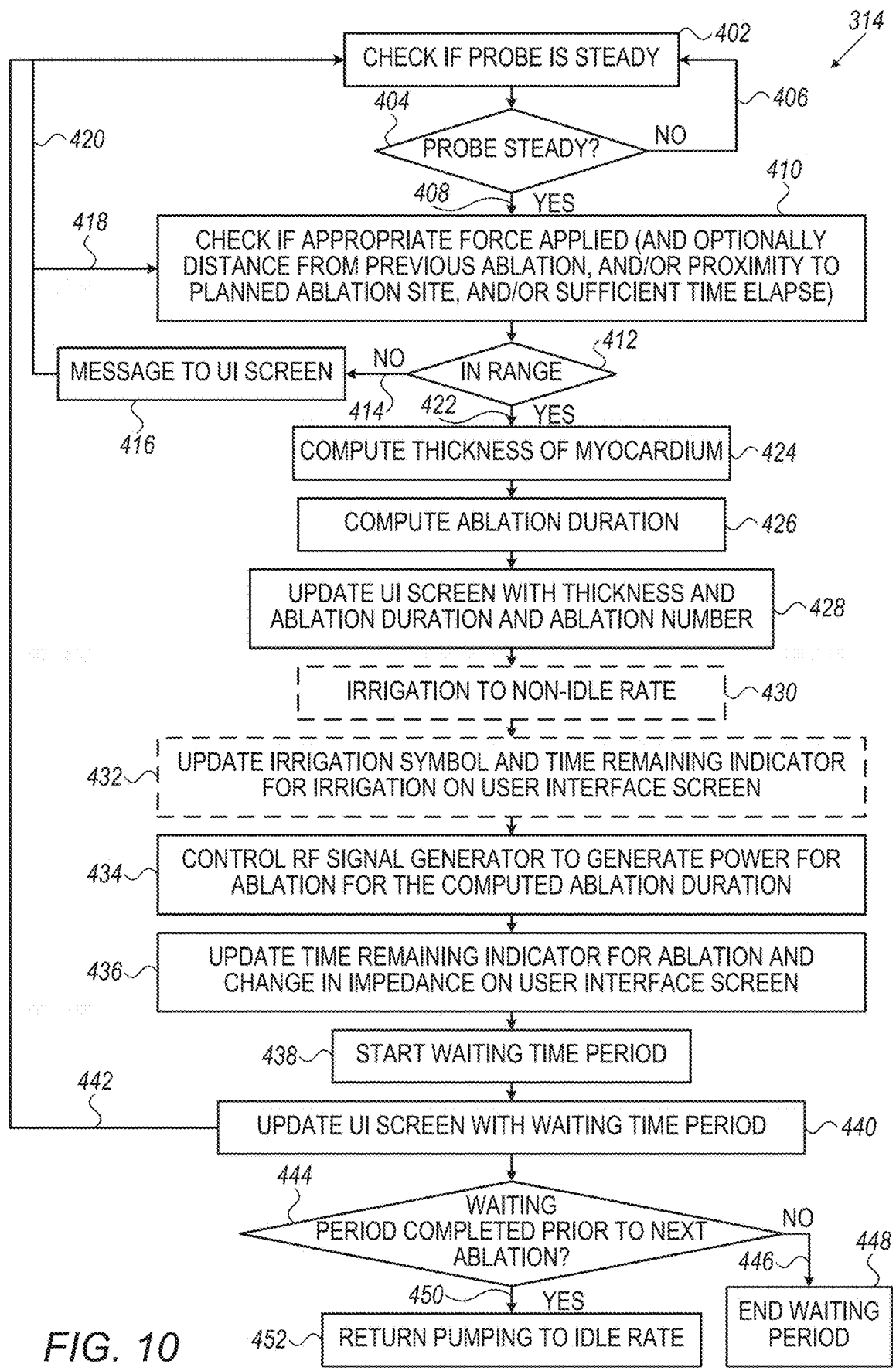
FIG. 10 is a flow chart including exemplary sub-steps included in the step of controlling the serial ablation procedure of FIG. 9.

Reference is now made to FIG. 10, which is a flow chart including exemplary sub-steps included in the step of controlling the serial ablation procedure (block 314) of FIG. 9. Reference is also made to FIGS. 1, 2, and 5.

The processor 46 is configured to check (block 402) whether the relative location and the relative orientation of the probe 20 are steady with respect to the heart to within a given tolerance for a given time period prior to the current ablation. The location may be considered steady if the probe 20 does not move more than a given distance (e.g., 1-4 mm) in the given time period. The orientation may be considered steady if the orientation does not change by more than a given orientation (e.g., 5-10 degrees) in the given time period. The given time period may be set to any suitable value (e.g., 0.5 to 3 seconds). The various tolerances may be configurable by an operator (e.g., the physician 14) to accommodate the preferences of the physician 14. In some embodiments, when the probe 20 is steady for the given time period, the processor 46 assumes that the steadiness of the probe 20 indicates that a new ablation site has been reached and further checks associated with reaching a new ablation site are performed. At a decision block 404, if the probe 20 is not steady (branch 406) the step of block 402 is repeated, generally after a short delay, e.g., after 0.05-0.3 seconds. If the probe 20 is steady (branch 408), the processor 46 performs (block 410) various checks described below.

The processor 46 is configured to check whether a force applied by the probe 20 to the myocardium 16 is within a given range (e.g., 5-25 grams) prior to permitting performance of the ablation. The given range may be set to any suitable values. The processor 46 is configured to check whether the relative location of the probe 20 is close enough to a planned ablation site (or ablation area or ablation line) prior to permitting performance of the ablation. This check is relevant if the physician 14 provided planned ablation sites, area(s), or line(s) prior to the serial ablation procedure. As a safety feature, the processor 46 is configured to check whether the relative location of the probe 20 is far enough away (e.g., at least 3-10 mm away) from a previous ablation site prior to permitting performance of the current ablation. The previous ablation may be an ablation performed prior (e.g., immediately prior) to the current ablation under consideration either in this serial ablation procedure or a different serial ablation procedure. As another safety feature, the processor 46 is configured to check whether sufficient time has elapsed (e.g., 30 second to 3 minutes) since a previous ablation prior to permitting performance of the current ablation. At a decision block 412, if any of the checks (described below) yield an out-of-range result (branch 414), the processor 46 may output (block 416) an appropriate message to the user interface screen 200. Processing may then continue along a line 418 repeating the step of block 410 or along a line 420 repeating the step of block 402 (for example, if the result of the check requires repositioning the probe 20). If the checks are all in-range (branch 422), the process continues with the step of block 424 described below.

In response to finding the probe 20 to be steady and the other checks providing an in-range result, the processor 46 is configured to automatically compute (block 424) a thickness of the myocardium 16 at the relative location of the current ablation and automatically compute (block 426) the ablation duration for the current ablation responsively to the computed thickness. Other methods may be used to estimate the thickness and the ablation duration. Similarly, the ablation duration may be computed using a method that is not based on thickness, such as based on the method described in US Patent Publication 2011/0152856 of Govari, et al.

The processor 46 is configured to update (block 428) (or generate and render) the user interface screen 200 with the computed thickness of the myocardium 16, the computed ablation duration, and the ablation number.

If the irrigation rate is at the idle rate (e.g., typically prior to the first ablation), the processor 46 is operative to control (block 430) the pump 65 to commence pumping at the non-idle rate. During the time period it takes to achieve the non-idle rate, the processor 46 is configured to update (block 432) (or generate and render) the user interface screen 200 showing the moving time indicator 216 (FIG. 5) moving along the line 218 indicative of the time elapsed during the time period and/or the time remaining until pumping at the non-idle rate is achieved. Once the irrigation has reached the non-idle rate, the processor 46 is configured to update the irrigation rate symbol 226 to reflect the non-idle rate.

The processor 46 is configured to automatically control (block 434) the RF signal generator 63 to generate the RF power for the computed ablation duration of the current ablation. The processor 46 is configured to update (block 436) (or generate and render) the user interface screen 200 showing the moving time indicator 216 (FIG. 6) moving along the line 218 indicative of the time elapsed during the ablation and/or the time remaining until the end of the ablation duration. The processor 46 is also configured to show the change in impedance using the colored area 210 and the impedance indicator 208 as the ablation progresses.

In some embodiments, the steps of blocks 424-428 may be performed after commencement of the step of block 434.

Once the ablation has been completed the processor 46 is configured to start (block 438) timing a waiting time period (e.g., 20 seconds to 4 minutes) of the waiting state that follows the ablation state in the serial ablation procedure.

The processor 46 is configured to update (block 440) (or generate and render) the user interface screen 200 showing the indicator 216 (FIG. 7) moving along the line 218 indicative of the time elapsed during the waiting time period and/or a waiting time remaining until the end of the waiting time period.

While the waiting time period is progressing, the processor 46 is configured to perform (arrow 442) the step of block 402 which checks if the probe 20 is steady thereby indicating that a new ablation site has been reached. The steps of the blocks after the block 402 are also performed according to the flow described above.

At decision block 444, the processor 46 is configured to check if the waiting time period has completed prior to a next ablation being performed. If the waiting time period has not completed prior to the next ablation being performed (i.e., an ablation has started prior to the end of the waiting time period (branch 446), the checking for the completion of the waiting time period ends (block 448) and the ablation state processing described above continues. If the waiting time period has completed prior to the next ablation starting (branch 450) (i.e., when a waiting time between adjacent ablations, e.g., between the current ablation and the next ablation, is greater than the given waiting time period), the processor 46 is configured to control (block 452) the pump 65 to return to pumping at the idle rate.

The steps of the blocks of FIG. 10 are performed cyclically until the serial ablation procedure is halted by the physician 14.

In practice, some or all of these functions may be combined in a single physical component or, alternatively, implemented using multiple physical components. These physical components may comprise hard-wired or programmable devices, or a combination of the two. In some embodiments, at least some of the functions of the processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. An ablation system comprising:
    a probe configured to be inserted into a chamber of a heart, the probe including an electrode configured to apply radiofrequency (RF) power to a myocardium in the chamber so as to ablate the myocardium;
    an RF signal generator configured to generate the RF power to be applied by the electrode to ablate the myocardium;
    a tracking module configured to compute a relative location and a relative orientation of the probe;
    a user interface comprising at least one user input device and a display; and
    a processor configured to:
        receive a signal from the at least one user input device indicating an actuation of a serial ablation procedure including performing a plurality of ablations over time at different locations of the myocardium; and
        control the serial ablation procedure responsively to receiving the signal so that for each one ablation of the plurality of ablations the processor is configured to: check whether the relative location and the relative orientation of the probe are steady to within a given tolerance for a given time period prior to the one ablation; automatically compute an ablation duration for the one ablation after finding the probe to be steady at the relative location; automatically control the RF signal generator to generate the RF power for the computed ablation duration of the one ablation; and render to the display a user interface screen including a plurality of indicators describing a state of the serial ablation procedure, the plurality of indicators including a time indicator indicating a time remaining until an end of the ablation duration at the relative location, wherein the probe includes an irrigation channel through which to irrigate the myocardium, the system further comprising a pump to pump an irrigation fluid into the irrigation channel at an idle rate and at least one non-idle rate being higher than the idle rate, the processor being configured to control the pump to return to pumping at the idle rate when a waiting time period between adjacent ones of the plurality of ablations is greater than a second given time period.

2. The system according to claim 1, wherein the processor is configured to: compute a thickness of the myocardium at the relative location of each ablation of the plurality of ablations responsively to the probe being steady; and compute the ablation duration for each ablation responsively to the computed thickness.

3. The system according to claim 1, wherein the processor is configured to check whether the relative location of the probe is far enough away from a previous ablation prior to permitting performance of the one ablation.

4. The system according to claim 3, wherein the previous ablation was performed immediately prior to a current ablation under consideration.

5. The system according to claim 3, wherein the previous ablation was performed in a different serial ablation procedure.

6. The system according to claim 1, wherein the processor is configured to check whether the relative location of the probe is close enough to a planned ablation site prior to permitting performance of each ablation of the plurality of ablations.

7. The system according to claim 6, wherein the processor is configured to receive a signal from the at least one user input device indicating selection of any one or more of the following: planned ablation sites, a planned ablation area, and a planned ablation line having respective locations on a map of the myocardium.

8. The system according to claim 1, wherein the processor is configured to check whether sufficient time has elapsed since a previous ablation prior to permitting performance of the one ablation.

9. The system according to claim 1, wherein the processor is configured to check whether a force applied by the probe to the myocardium is within a given range prior to permitting performance of each ablation of the plurality of ablations.

10. The system according to claim 1, wherein the processor is configured to halt the serial ablation procedure responsively to not receiving the signal from the at least one user input device.

11. The system according to claim 1, wherein the processor is configured to generate, and render to the display, the user interface screen showing an indicator moving along a line indicative of the time remaining until an end of the waiting time period.

12. The system according to claim 1, wherein the probe includes a temperature sensor configured to provide a temperature signal which is indicative of a temperature of the myocardium at a plurality of different times, the processor being configured to generate, and render to the display, the user interface screen showing a colored area having a color indicative of the temperature of the myocardium.

13. The system according to claim 1, wherein the processor is configured to generate, and render to the display, the user interface screen showing a colored area having a color indicative of an impedance measurement of the myocardium.

14. The system according to claim 1, wherein the processor is configured to generate, and render to the display, the user interface screen showing an indicator moving along a line indicative of the time remaining until the end of the ablation duration.

15. The system according to claim 1, wherein the processor is configured to generate, and render to the display, the user interface screen showing any one or more of the following: a temperature of the myocardium; an impedance of the myocardium; a change in the impedance of the myocardium; the ablation duration; a thickness of the myocardium; an irrigation rate symbol; and an ablation number in the serial ablation procedure.

16. An ablation method comprising:
computing a relative location and a relative orientation of a probe configured to be inserted into a chamber of a heart, the probe including an electrode configured to apply radiofrequency (RF) power to a myocardium in the chamber so as to ablate the myocardium;
receiving a signal from at least one user input device indicating an actuation of a serial ablation procedure including performing a plurality of ablations over time at different locations of the myocardium; and
controlling the serial ablation procedure responsively to receiving the signal so that for each one ablation of the plurality of ablations the following are performed:
checking whether the relative location and the relative orientation of the probe are steady to within a given tolerance for a given time period prior to the one ablation;
automatically computing an ablation duration for the one ablation after finding the probe to be steady at the relative location;
automatically controlling the RF signal generator to generate the RF power for the computed ablation duration of the one ablation; and
rendering to a display a user interface screen including a plurality of indicators describing a state of the serial ablation procedure, the plurality of indicators including a time indicator indicating a time remaining until an end of the ablation duration at the relative location, the method further comprising pumping an irrigation fluid into an irrigation channel of the probe at an idle rate and at least one non-idle rate being higher than the idle rate; and
controlling pumping of the irrigation rate to return to pumping at the idle rate when a waiting time period between adjacent ones of the plurality of ablations is greater than a second given time period.

17. The method according to claim 16, further comprising computing a thickness of the myocardium at the relative location of each ablation of the plurality of ablations responsively to the probe being steady, wherein computing the ablation duration includes computing the ablation duration for each ablation responsively to the computed thickness.

18. The method according to claim 16, further comprising checking whether the relative location of the probe is far enough away from a previous ablation prior to permitting performance of the one ablation.

19. The method according to claim 18, wherein the previous ablation was performed immediately prior to a current ablation under consideration.

20. The method according to claim 18, wherein the previous ablation was performed in a different serial ablation procedure.

21. The method according to claim 16, further comprising checking whether the relative location of the probe is close enough to a planned ablation site prior to permitting performance of each ablation of the plurality of ablations.

22. The method according to claim 21, further comprising receiving a signal from the at least one user input device indicating selection of any one or more of the following: planned ablation sites, a planned ablation area, and a planned ablation line, having respective locations on a map of the myocardium.

23. The method according to claim 16, further comprising checking whether sufficient time has elapsed since a previous ablation prior to permitting performance of the one ablation.

24. The method according to claim 16, further comprising checking whether a force applied by the probe to the myocardium is within a given range prior to permitting performance of each ablation of the plurality of ablations.

25. The method according to claim 16, further comprising halting the serial ablation procedure responsively to not receiving the signal from the at least one user input device.

26. The method according to claim 16, further comprising generating, and rendering to the display, the user interface screen showing an indicator moving along a line indicative of the time remaining until an end of the waiting time period.

27. The method according to claim 16, further comprising:
providing a temperature signal which is indicative of a temperature of the myocardium at a plurality of different times; and
generating, and rendering to the display, the user interface screen showing a colored area having a color indicative of the temperature of the myocardium.

28. The method according to claim 16, further comprising generating, and rendering to the display, the user interface screen showing a colored area having a color indicative of an impedance measurement of the myocardium.

29. The method according to claim 16, further comprising generating, and rendering to the display, the user interface screen showing an indicator moving along a line indicative of the time remaining until the end of the ablation duration.

30. The method according to claim 16, further comprising generating, and rendering to the display, the user interface screen showing any one or more of the following: a temperature of the myocardium; an impedance of the myocardium; a change in the impedance of the myocardium; the ablation duration; a thickness of the myocardium; an irrigation rate symbol; and an ablation number in the serial ablation procedure.

* * * * *